United States Patent [19]

Tokarek et al.

[11] Patent Number: 5,114,397
[45] Date of Patent: May 19, 1992

[54] APPARATUS FOR REMOVING METAL FRAGMENTS FROM THE EYE

[76] Inventors: Ronald F. Tokarek, Box 5112, Stn E. Edmonton, Alberta, Canada, T5P 4C1; Wesley E. Herman, 10305 - 109 Ave., Edmonton, Alberta T5M 2G7, Canada

[21] Appl. No.: 533,834

[22] Filed: Jun. 6, 1990

[30] Foreign Application Priority Data

Jun. 14, 1989 [CA] Canada .................... 602717

[51] Int. Cl.⁵ ............................................. A61B 17/52
[52] U.S. Cl. ........................................ 600/11; 606/162
[58] Field of Search .................. 600/9, 11, 12, 13; 606/106, 107, 162

[56] References Cited

U.S. PATENT DOCUMENTS

| | | | |
|---|---|---|---|
| 2,390,339 | 12/1945 | Ullman et al. | 600/11 X |
| 2,436,538 | 2/1948 | Wing, Sr. | 600/11 |
| 3,656,481 | 4/1972 | Ness | 600/11 X |

OTHER PUBLICATIONS

Toronto Globe & Mail, "New Tools Retrieve Swallowed Pins, Nails", Dec. 31, 1963.

Primary Examiner—Kyle L. Howell
Assistant Examiner—Kevin Pontius
Attorney, Agent, or Firm—Anthony R. Lambert

[57] ABSTRACT

An apparatus for removing metal fragments from the eye which consists of a magnetic probe.

4 Claims, 4 Drawing Sheets

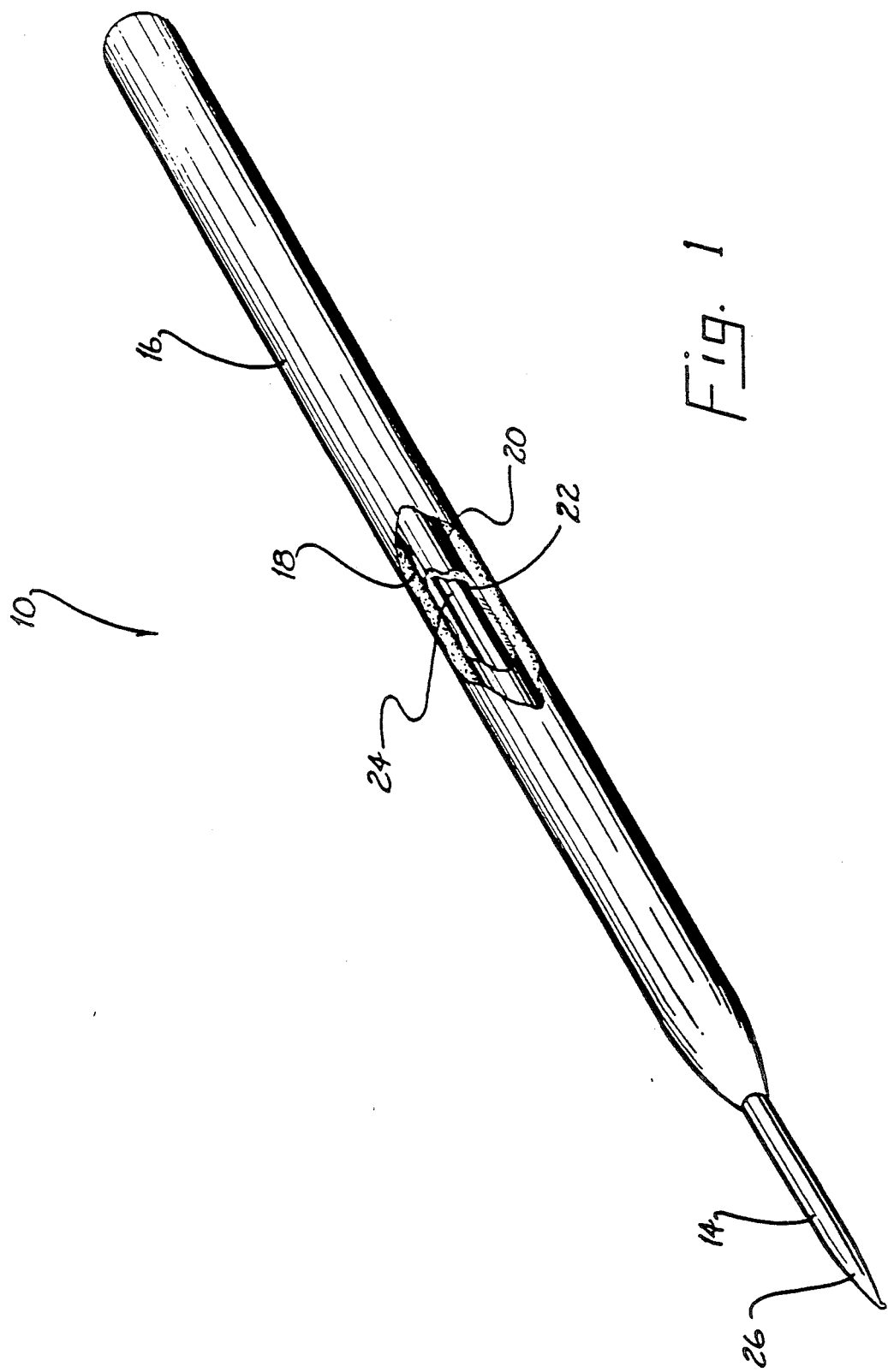

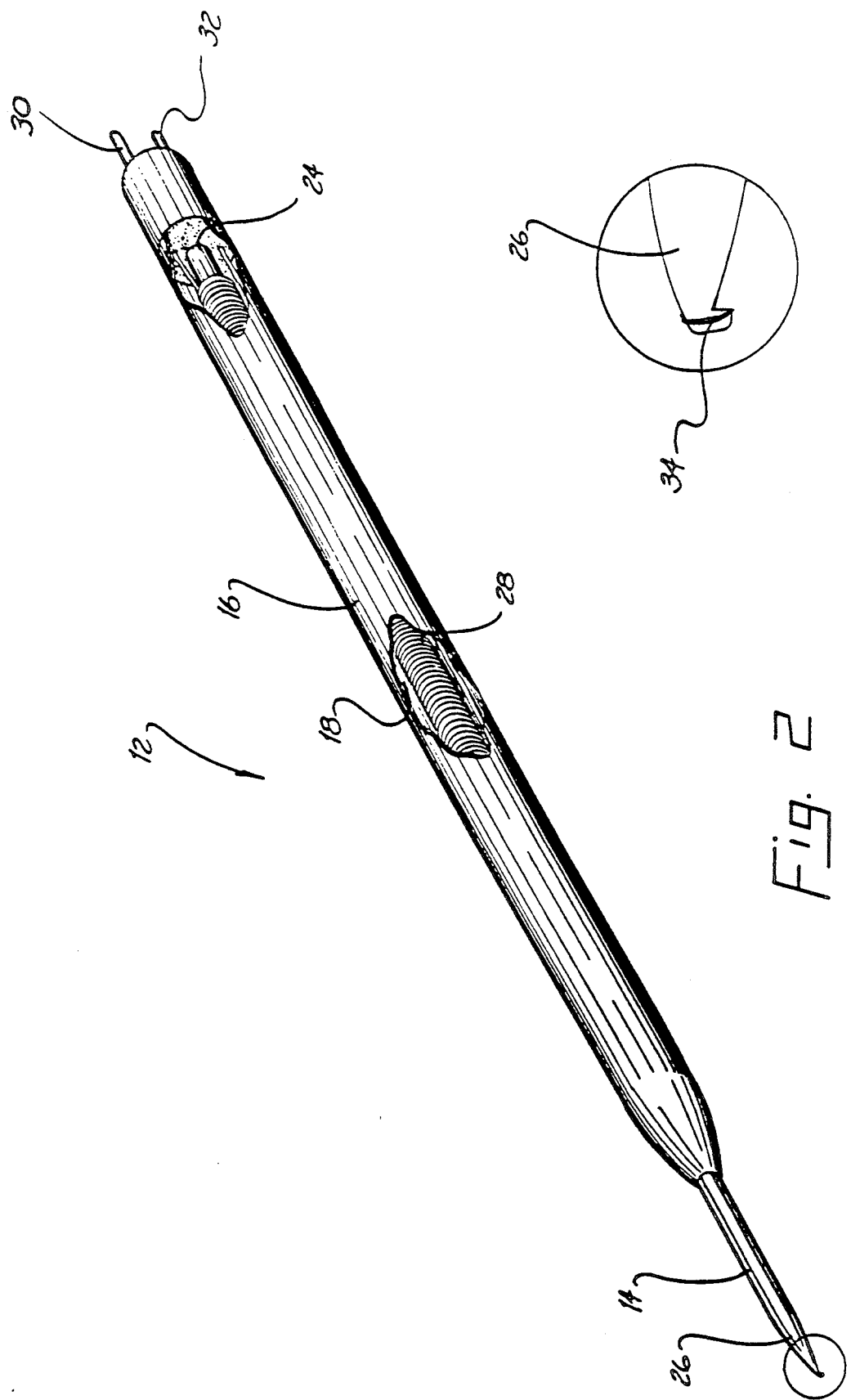

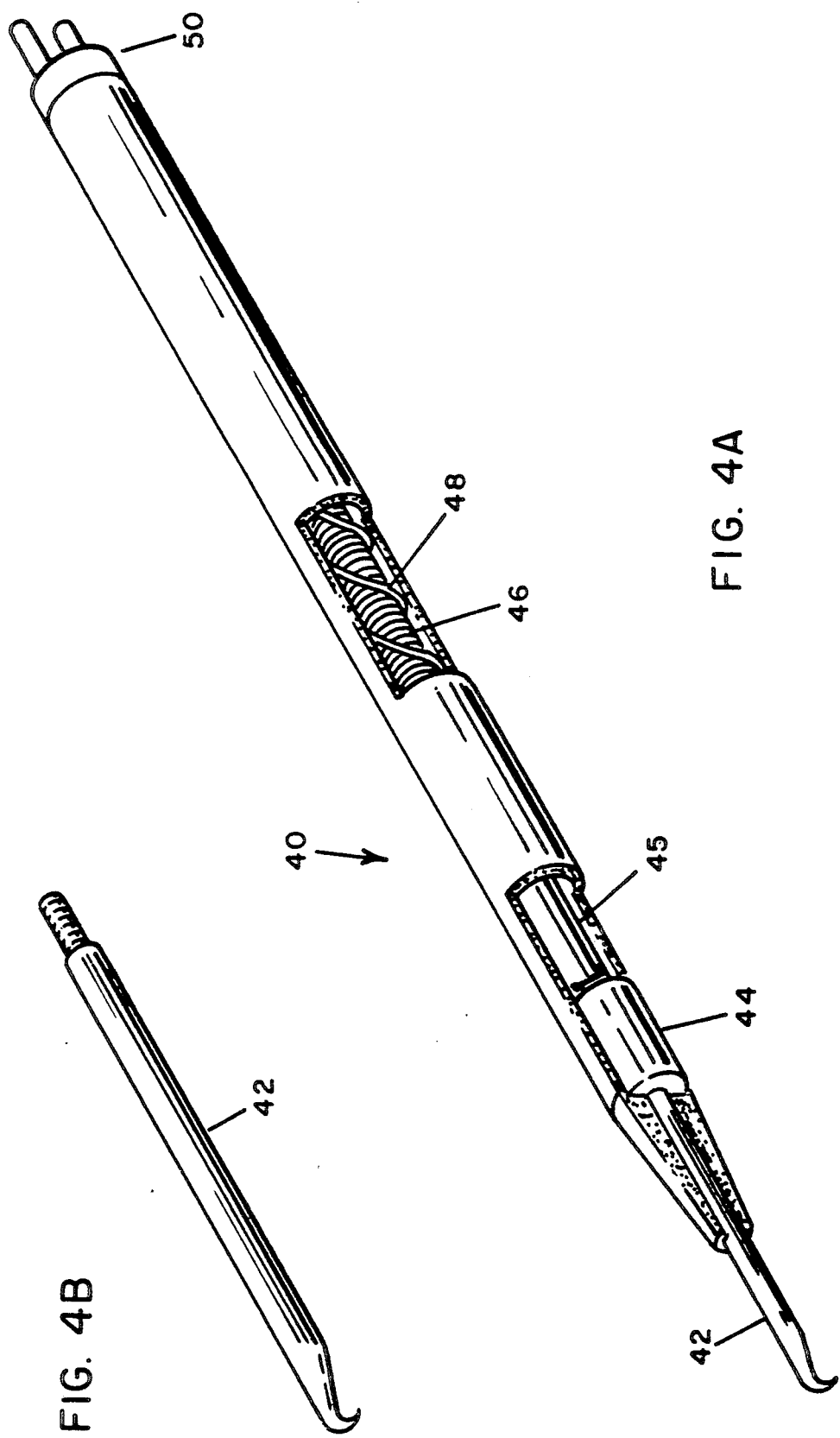

APPARATUS FOR REMOVING METAL FRAGMENTS FROM THE EYE

FIELD OF INVENTION

This invention relates to an apparatus for removing metal fragments from the eye.

BACKGROUND OF THE INVENTION

One of the most common type of eye injuries is that of having a foreign body in the eye. A large proportion of the foreign bodies are metallic fragments. At the present time the eye is anaesthetized, a coloured dye is placed in the eye to assist in locating the fragment, and the physician uses a needle or syringe to remove the fragment. With the needle the physician picks at the fragment. With the syringe the fragment is drawn out of the eye. Often a combination of these techniques is used. The fragments are difficult to remove and the treatment can result in further irritation or injury to the eye.

SUMMARY OF THE INVENTION

What is required is an apparatus for removing metal fragments from the eye which will minimize irritation to the eye during the removal procedure.

According to the invention there is provided an apparatus for removing metal fragments from the eye which is comprised of a magnetic probe.

BRIEF DESCRIPTION OF THE FIGURES

These and other features of the invention will become more apparent from the following description in which reference is made to the appended drawings, wherein:

FIG. 1 is a partially cut away perspective view of a first embodiment of the invention.

FIG. 2 is a partially cut away perspective view of a second embodiment of the invention.

FIG. 3 is a detailed view of a portion of the apparatus illustrated in FIG. 2.

FIG. 4 A is a partially cut away perspective view of a third embodiment of the invention.

FIG. 4B shows a close up of a tip of an embodiment of the invention.

DETAILED DESCRIPTION OF PREFERRED EMBODIMENTS

Figures 5, 6:
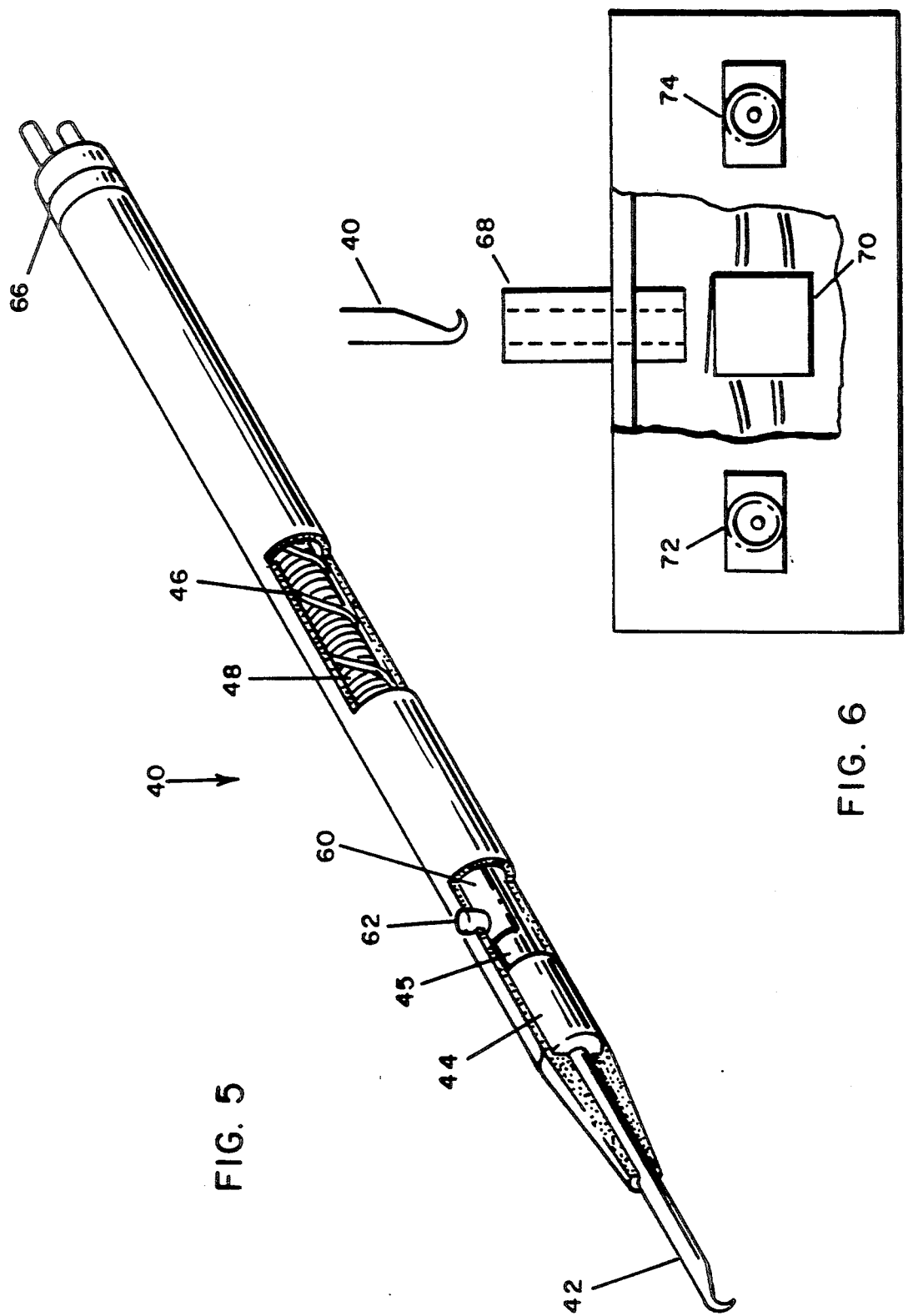
FIG. 5 is a partially cut away perspective view of the third embodiment of the invention.
FIG. 6 is a cross-section of a holder for the embodiment of FIGS. 4 and 5.

A preferred embodiment will now be described with reference to FIGS. 1 through 3. The first embodiment, generally designated by reference numeral 10, and the second embodiment, generally designated by reference numeral 12 are apparatus for removing metal fragments from the eye. Both embodiments 10 and 12 create a magnetic field within a ferromagnetic probe 14. The primary distinction between first embodiment 10 and second embodiment 12 lies in the means used for transmitting a magnetic field through the ferromagnetic probe 14.

First embodiment 10 is illustrated in FIG. 1. Embodiment 10 has a non-magnetic cylindrical casing 16. Casing 16 has a hollow interior 18. An elongate magnet 20 is positioned within interior 18 of casing 16. Magnet 20 has a central cavity 22. Ferromagnetic probe 14 has one end 24 extending into central cavity 22 of magnet 20. An opposed working end 26 of probe 14 protrudes from casing 16.

In order to use the first embodiment 10, the physician merely brings working end 26 of probe 14 into contact with a metal fragment. The probe relies upon the magnetic attraction between the probe and the metal fragment for its effective operation.

The second embodiment 12 is illustrated in FIG. 2. Embodiment 12 has a non-magnetic cylindrical casing 16. Casing 16 has a hollow interior 18. Ferromagnetic probe 14 has one end 24 which extends into interior 18 of casing 16. An opposed working end 24 of probe 14 protrudes from casing 16. A conductive wire 28 which is coated with insulating material is coiled around probe 14. Wire 28 has ends 30 and 32 which can be connected to a power source (not shown).

In order to use the second embodiment 12, the physician connects ends 30 and 32 of wire 28 to a power source (not shown) such as a battery. Upon connection of wire 28 to a power source probe 14 becomes an electromagnet. The physician brings working end 26 of probe 14 into contact with a metal fragment. The probe relies upon the magnetic attraction between the probe and the metal fragment for its effective operation. Wire 28 is coated to reduce the amount of heat which is generated by the flow of current.

In some instances the metal fragment becomes embedded in the eye to such an extent that magnetic force alone will not remove the fragment. The inventors, therefore, prefer to equip working end 26 of probe 14 with a barb 34, as illustrated in FIG. 3. The inventors have found barb 34 to be the most effective way to manipulate a metal fragment to dislodge the same to a sufficient extent that the magnetic force provided by the embodiment 10 or 12 will remove the same.

FIGS 4A and 4B shows a third embodiment of the probe with a disposable tip 42 that screws into a brass bushing 44. The brass bushing 44 butts up to a steel rod 45 that is doubly wrapped in a pair of wires 46 and 48, each forming independent circuits. Plug 50 connects to a power source (not shown). The number of turns and the choice of the wires depends on the desired degree of magnetic force required. 22 gauge magnet wire, readily commercially available, may be used for both of the primary and secondary coils 46 and 48. The tip 42 is preferably nickel plated steel, readily commercially available. The tip 42 may be barbed for ease in retrieving metal fragments.

The barb may also be used to retrieve other foreign particulates such as glass or wood.

FIG. 5 shows the same embodiment as shown in FIG. 4 except that it includes a printed circuit board 60 and push-button switch 62 for selectively providing power to the pair of wires 46 and 48. By this means, one or the other or both of the wires may be provided power, so that the magnetic flux in the probe may be altered as desired. An electrical connector is also provided for coupling to a power source. The printed circuit board 60 is a simple coil switcher.

FIG. 6 shows a holder for the embodiment of the probe shown in FIGS. 4 and 5. Housing 76 includes a probe holder 68 which receives the probe 40, and a pressure switch 70 which turns the power to the probe off when the probe is in the holder 68. Power to the holder is provided through inlet jack 72, and output to the probe 40 through outlet jack 74. The power supply (not shown) may be for example 120 volts AC, 60 Hz, 4 W., DC-Pack (tm) AC adapter model no. QFK-620B2 available from Radio Shack or the equivalent. It will be apparent to one skilled in the art that the present invention minimizes irritation to the eye during the removal procedure. In some cases the physician will be able to remove the metal fragment by merely placing the probe in proximity with the fragment. It will also be apparent to one skilled in the art that modifications may be made to the embodiments shown without departing from the spirit and scope of the invention. For example, the inventors contemplate having working end 26 of probe 14 disposable in order to ensure that the instrument placed in the patients eye is always sterile. The inventors also contemplate other means of creating and maintaining a magnetic charge in probe 14.

We claim:

1. An apparatus for removing metal fragments from the eye comprising:
    a magnetizable probe having a working end;
    means for transmitting a magnetic field through the magnetizable probe to the working end;
    the working end including a tip end having reduced diameter; and
    a barb formed at the tip end of the magnetizable probe.

2. The apparatus of claim 1 in which the means for transmitting a magnetic field through the magnetizable probe includes:
    a non-magnetic cylindrical casing having a hollow interior;
    an elongate magnet disposed within the interior of the casing, the magnet having a central cavity; and
    the magnetizable probe having one end extending into the central cavity of the magnet, and the working end protruding from the casing.

3. The apparatus of claim 1 in which the means for transmitting a magnetic field through the magnetizable probe includes:
    a non-magnetic cylindrical casing having a hollow interior;
    the magnetizable probe having one end extending into the interior of the casing and the working end protruding from the casing; and
    a conductive wire being coiled around the probe such that upon connection of the wire to a power source the probe becomes an electromagnet.

4. An apparatus for removing metal fragments from the eye comprising:
    a magnetic probe having a working end, the working end having a tip end of reduced diameter; and
    a barb formed at the tip end of the magnetic probe.

* * * * *